United States Patent [19]

Vinegar et al.

[11] Patent Number: 4,671,102

[45] Date of Patent: Jun. 9, 1987

[54] METHOD AND APPARATUS FOR DETERMINING DISTRIBUTION OF FLUIDS

[75] Inventors: Harold J. Vinegar; Daniel J. O'Meara, Jr., both of Houston; John A. Rohan, Rosenberg, all of Tex.

[73] Assignee: Shell Oil Company, Houston, Tex.

[21] Appl. No.: 746,225

[22] Filed: Jun. 18, 1985

[51] Int. Cl.⁴ .............................................. G01N 15/00
[52] U.S. Cl. ................................... 73/61.1 R; 73/38; 250/573; 356/427; 378/52
[58] Field of Search ..................... 73/61.4, 61.1 R, 38; 356/426, 427; 250/573, 575, 253, 255; 378/52

[56] References Cited

U.S. PATENT DOCUMENTS

| | | | |
|---|---|---|---|
| 3,009,388 | 11/1961 | Polanyi | 73/61.4 |
| 3,679,367 | 7/1972 | Negersmith et al. | 73/61.4 |
| 3,683,674 | 8/1972 | Roy | 73/38 |
| 3,684,450 | 8/1972 | Alder et al. | 73/61.4 |
| 4,452,902 | 6/1984 | Suovaniemi et al. | 356/427 |
| 4,567,373 | 1/1986 | O'Meara, Jr. et al. | 356/427 X |

FOREIGN PATENT DOCUMENTS

| | | | |
|---|---|---|---|
| 2727400 | 12/1978 | Fed. Rep. of Germany | 73/61.4 |
| 111741 | 7/1983 | Japan | 73/61.4 |
| 160843 | 9/1983 | Japan | 73/61.4 |
| 165040 | 9/1983 | Japan | 73/61.4 |

OTHER PUBLICATIONS

Hassler, G. L. and Brunner, E., Measurement of Capillary Pressures in Small Core Samples, Trans. AIME 1945, vol. 160, p. 114.
Hagoort, J., Oil Recovery by Gravity Drainage, Soc. Pet. Eng. J., 1980, vol. 20, p. 139.

Primary Examiner—Stewart J. Levy
Assistant Examiner—Hezron E. Williams

[57] ABSTRACT

Method and apparatus are provided to determine the distribution of fluids in a sample employing a centrifuge. The apparatus is an automated centrifuge which may employ a plurality of X-ray energies to determine a two-dimensional image of the saturation of multiple fluids in a sample. The saturation images may be used to calculate a capillary pressure curve or relative permeability curve for a borehole core sample. The X-ray source may be selectively synchronized with at least one of the rotating specimen holders to allow for preselection of which specimen holder is to be imaged by the X-ray energies. The method images a sample in a plurality of points during centrifuging to determine fluid distributions in the sample. Alternative automated centrifuges are provided which may also measure resistivity during centrifuging and may have the source and detector located on the sample holder.

26 Claims, 14 Drawing Figures

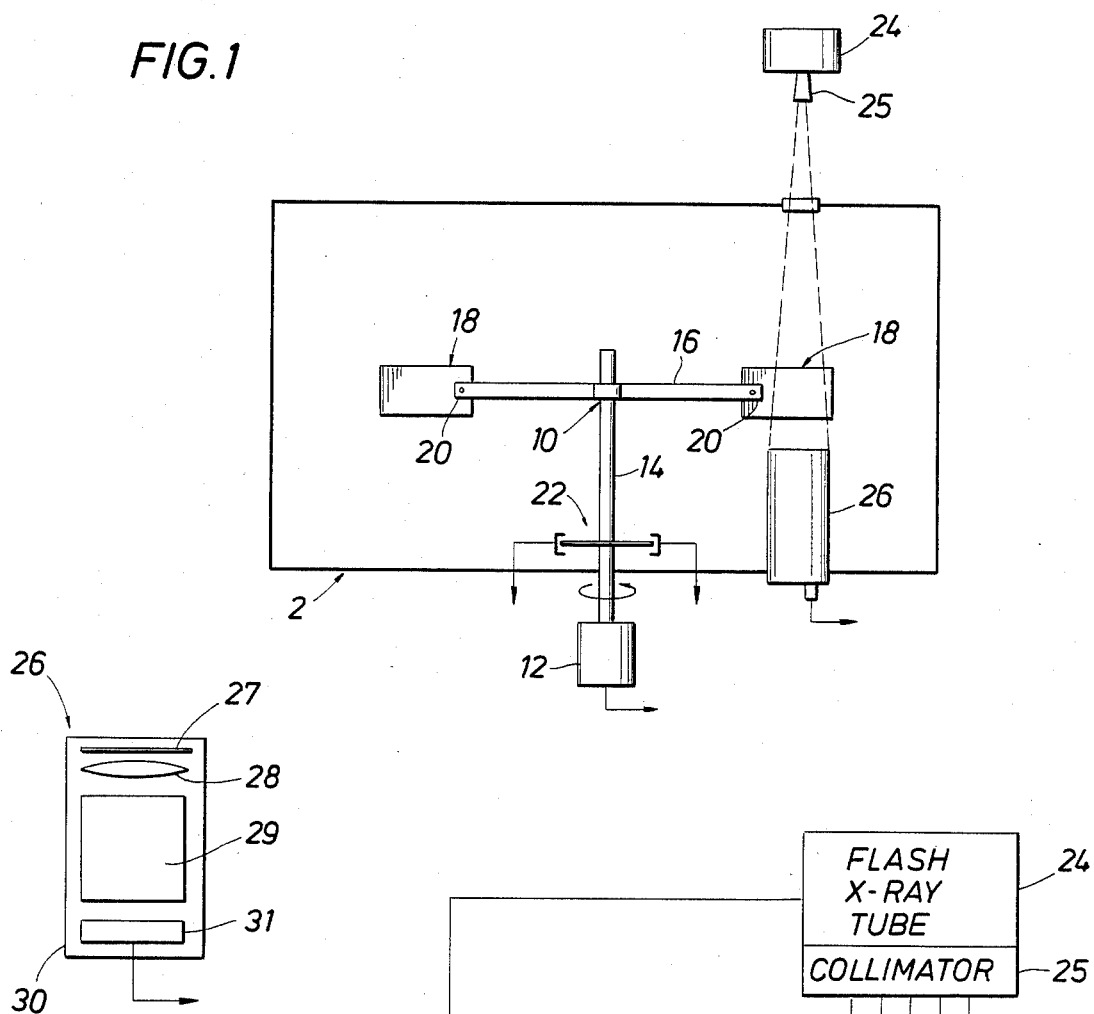
FIG. 1
FIG. 1A
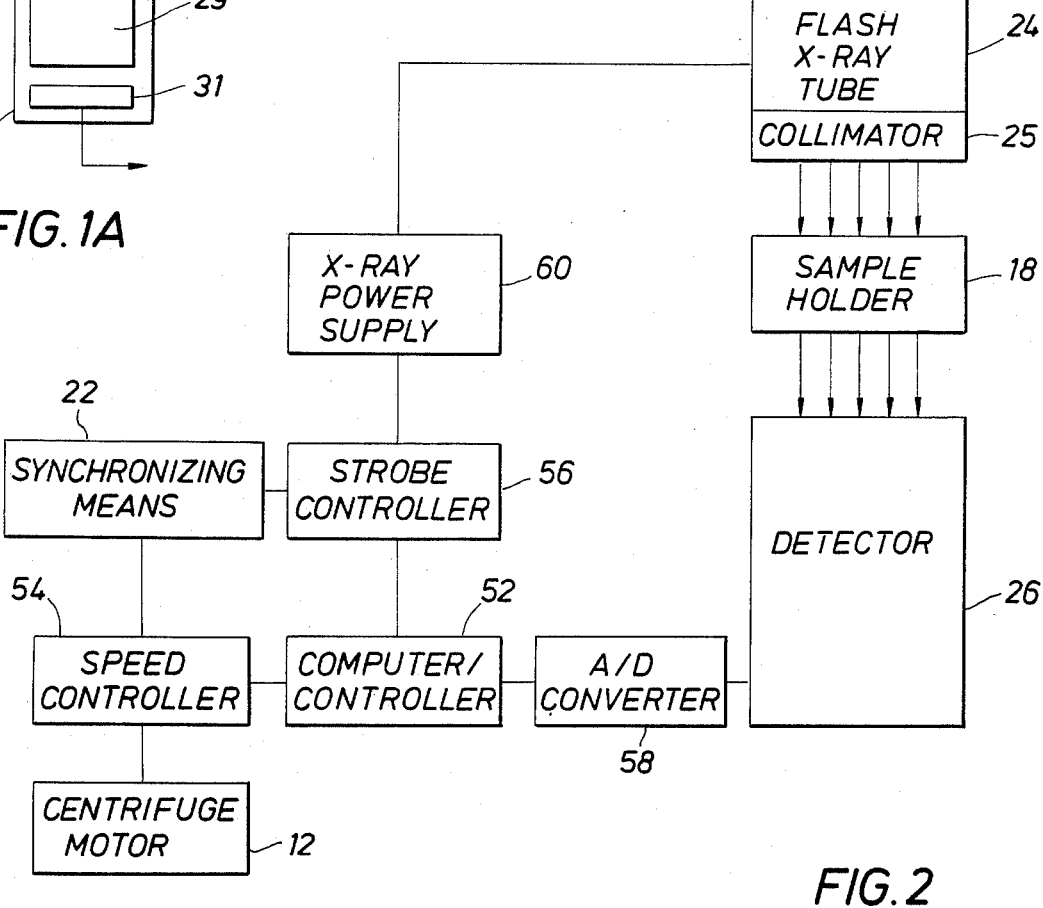
FIG. 2

METHOD AND APPARATUS FOR DETERMINING DISTRIBUTION OF FLUIDS

BACKGROUND OF THE INVENTION

This invention relates to centrifuges and more particularly, relates to automated centrifuges.

The oil industry has developed several methods for measuring capillary pressure and relative permeability of reservoir core samples using centrifuges. Capillary pressure and relative permeability are important properties for describing the flow of fluids in porous media and are generally needed in the reservoir engineering of an oil field. These properties help the reservoir engineer determine, for example, the productivity of a reservoir, the total reserves, and the likelihood of success for various oil recovery processes, such as water flooding or carbon dioxide flooding.

One of the preferred methods for measuring capillary pressure is the centrifuge method of Hassler and Brunner (Hassler, G. L. and Brunner, E., "Measurement of Capillary Pressures in Small Core Samples", Trans. AIME 1945, Vol. 160, pp 114). Similarly, a preferred method for measuring relative permeability is the centrifuge method of Hagoort (Hagoort, J., "Oil Recovery by Gravity Drainage", Soc. Pet. Eng. J., 1980, Vol. 20, p. 139).

These methods have the advantage of much greater speed compared to other methods for measurement and are amenable to automation. For both centrifuge methods, the core samples are mounted in special holders having glass collection tubes to allow for monitoring the production of fluid from the core samples. The cores are centrifuged and the effluent fluids from the samples are collected in the tubes. A strobed light source is used to determine the amounts of fluids collecting in the glass collection tubes.

Measuring the capillary pressure with the method of Hassler and Brunner requires increasing the speed of the centrifuge in "steps" or increments and measuring the amount of fluid produced from the core sample when all flow has ceased for that step (i.e. centrifuge speed) before increasing the centrifuge speed to the next "step". Measuring the relative permeability with the method of Hagoort requires running the centrifuge at a single speed, which is high enough to overwhelm capillary pressure effects, and measuring the amount of fluid produced from the core sample as a function of time.

In general, however, the capillary pressure or relative permeability curve determined by the prior art in a centrifuge experiment use effluent data alone. Since no measurements are made of the fluid saturations inside the core, various assumptions must be made concerning boundary conditions, uniformity of the displacement of the fluid, and homogeneity of the core. These assumptions may not always be valid, leading to inaccurate and unreliable results. However, even if these assumptions are valid, capillary pressure and relative permeability influence the measurement of each other.

The Hassler and Brunner method for measuring capillary pressure is confined to a drainage mode of flow for a water-wet core initially filled with a wetting fluid which is then invaded by a non-wetting fluid, i.e., oil invading a water-wet core. The method of Hassler and Brunner is not useful when a wetting fluid invades a water-wet core containing a non-wetting fluid as the equilibrium level of production of the non-wetting fluid is dependent upon imbibition and not centrifuge speed. However, such measurements are needed in order to design waterflood recovery methods where the invading fluid is wetting.

These and other limitations and disadvantages of the prior ar are overcome by the present invention however, and improved methods and apparatus are provided for centrifuging core specimens that are capable of determining fluid saturations inside the core specimen.

SUMMARY OF THE INVENTION

In a preferred embodiment of the present invention methods and apparatus are provided to determine fluid saturations inside a sample. The preferred method employs electromagnetic radiation to image a sample while it is being centrifuged, from which linear attenuation coeificients and fluid saturations may be calculated at a plurality of points in the sample. The fluid saturations may be employed to calculate capillary pressure or relative permeability.

In a preferred embodiment of the present invention an automated centrifuge apparatus is provided. Although X-ray radiation is preferred, other wavelengths of electromagnetic radiation may also be employed in embodiments of the present invention. The X-ray apparatus preferably has a flash X-ray tube mounted above the centrifuge so that a rotating sample may pass through the X-ray beam from this X-ray source. The flash X-ray tube may be synchronized with the rotational speed and rotation of the centrifuge so that the X-ray tube is energized and emits a pulsed X-ray beam when a preselected sample holder has rotated into a position directly below the X-ray tube and is of a short enough duration that the sample is effectively "frozen" in this position, i.e. does not move very much while exposed to the X-ray beam. The X-ray tube voltage is sufficiently high to provide an X-ray beam of sufficient energy to penetrate both the sample holder and sample without significant attenuation.

Further, the X-ray tube may be pulsed a plurality of times during the centrifuging process to obtain a series of X-ray pictures of the fluid displacement with respect to time within the sample. A suitable detector may be located on the side of the sample holder opposite the X-ray tube so that the X-ray beam transmitted through the holder and sample may be detected. This detector is preferably a fluorescent screen and emits light. Light emitted from the fluorescent screen may be optically focused by a lens or fiber optic cables onto optical detection means. Alternatively, the X-ray tube may be below the centrifuge and the screen or any other type of detector means located above the centrifuge.

The intensity of the image measured by the optical detection means may be digitized into a two-dimensional array of intensity values which may be transmitted to a computer. That is, the sample is imaged in a plurality of points (in two dimensions) to determine fluid positions and their movements in small increments. A computer may store the information and may also provide a real time display on a CRT so that the operator can observe the displacement process and alter the experimental conditions if necessary. In addition, the computer may convert the intensity information into fluid saturations, using information supplied on the thickness of the sample and previously measured linear attenuation coefficients for each of the fluids in the sample. The computer may then generate a saturation image of the sample from each digitized image.

Alternatively, the X-ray tube may be a constant source of X-rays, such as a rotating anode X-ray tube, rather than a flash X-ray tube. For a constant source X-ray tube, the detector is strobed to detect energy only when the preselected sample holder and sample are between the X-ray tube and detector means.

For two-phase flow measurements, preferably only a single X-ray energy is used to obtain the fluid saturations. However, for studies of three-phase flow, independent measurements must be made at two or more X-ray energies. Thus, an alternative embodiment of the present invention employs at least two or more X-ray energies to measure three-phase flow. These multiple X-ray energies may be obtained with two X-ray tubes operated at different peak acceleration voltages, or may be obtained from a single X-ray tube (operated at two voltages), or by employing a single X-ray tube and a dual energy detector sensitive to two different energies from this X-ray tube (alternatively two such X-ray tubes could be employed with such a dual energy detector), or by employing a mechanical X-ray filter (such as a rotating wheel containing two different filters).

It is an object of the present invention to obtain images of multiphase fluid saturation distributions within a sample.

It is another object of the present invention to provide an automated centrifuge capable of determining saturation distributions within an inhomogeneous sample.

It is also an object of the present invention to provide an automated centrifuge capable of subjecting a sample to high pressures and high temperatures during centrifuging to determine fluid distributions within the sample.

It is also an object of the present invention to provide animated movies of saturations of fluids in a core during displacement processes.

It is also an object of the present invention to provide apparatus for measuring resistivity and fluid saturation of a sample.

It is also an object of the present invention to provide apparatus for measuring capillary pressure or relative permeability in a sample.

It is a specific object of the present invention to provide a method for measuring the distribution of fluids in a sample, comprising, centrifuging said sample, and periodically imaging said sample in a plurality of points during centrifuging.

It is also a specific object of the present invention to provide apparatus for measuring the distribution of fluids in a sample, comprising, a centrifuge having a predetermined number of sample holders for containing said sample and capable of operating at a plurality of speeds, a source of electromagnetic energy positioned to radiate onto at least one preselected holder as it passes adjacent said source, a detector array positioned to detect electromagnetic energy transmitted through said at least one preselected holder, synchronizing means for preselecting said at least one preselected holder, recorder means for recording signals from said detector array, and controller means for controlling said synchronizing means, said recorder means, and the operating speed of said centrifuge.

It is also a specific object of the present invention to provide an apparatus for measuring the distribution of fluids in a sample, comprising, a centrifuge having a predetermined number of sample holders for containing said sample and capable of operating at a plurality of speeds, a source of electromagnetic energy positioned adjacent at least one preselected holder to irradiate said preselected holder, and a detector array positioned adjacent said at least one preselected holder and opposite said source to detect electromagnetic energy transmitted through said at least one preselected holder.

These and other features and objects of the present invention will become apparent from the following detailed description wherein reference is made to the Figures in the accompanying drawings.

BRIEF DESCRIPTION OF THE DRAWINGS

FIG. 1 shows a side view, partially in cross section, of an X-ray centrifuge of the present invention.

Figure 1A shows an enlarged cross-section of a portion of the apparatus depicted in FIG. 1.

FIG. 2 shows a schematic block diagram of one embodiment of the present invention.

DETAILED DESCRIPTION OF THE PREFERRED EMBODIMENTS

Figure 3:
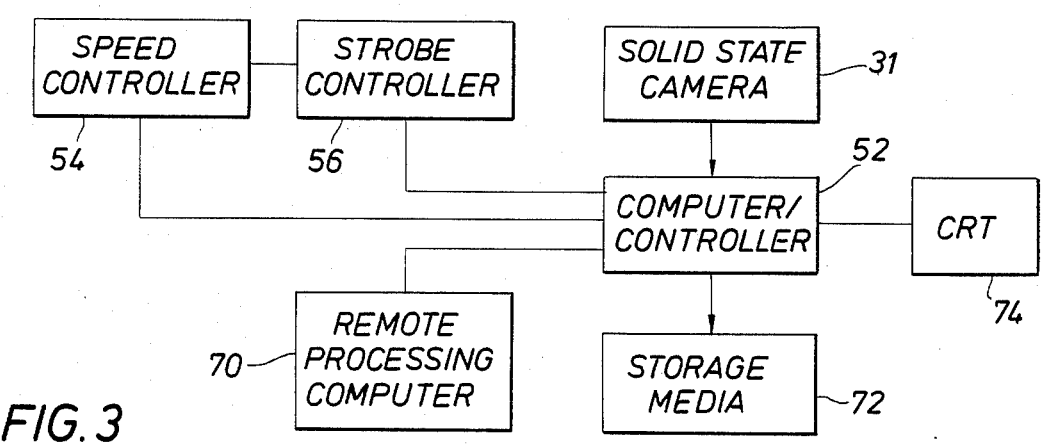
FIG. 3 shows a block diagram of an alternate embodiment of the apparatus of the present invention.

Referring now to FIG. 1, there may be seen a side view, partially in cross-section, of the apparatus 2 of the present invention. More particularly, there may be seen a conventional centrifuge 10, such as, for example, but not limited to model DPR 6000, available from International Equipment Company, Needham Heights, Mass., or model L8-55 M/P, available from Beekman Instruments, Inc. of Fullerton, Calif. This conventional centrifuge 10 consists of a motor 12, which drives the shaft 14. Shaft 14 is connected to rotor 16, which holds sample holders 18 by any suitable means, such as, for example but not limited to pins 20. Sample holders 18, in turn, may contain the samples (not shown) to be centrifuged. Centrifuge 10 may also contain a suitable synchronizing means 22 on shaft 14.

A source of electromagnetic energy 24, such as for example, but not limited to an X-ray tube (preferably such as flash X-ray tube HP 1500, or HP 43733A sold by Hewlett-Packard Company of McMinnville, Oreg.) is positioned adjacent centrifuge 10 so that the radiation or X-rays emitted therefrom may be collimated by lead collimator 25 and then impinge on the sample holder 18, which may contain a sample (not shown). A flash X-ray tube emits a burst of X-rays in approximately 30 nanoseconds with an intensity of about 60 milliroentgens at 1 meter. This short duration burst of X-rays (which is 100 times faster than optical strobes) is sufficiently fast that the motion of the centrifuge is effectively frozen, or stopped, during the time the X-ray energy passes through a core sample and/or holder 18. Such a quick burst of X-ray or other radiation allows for effectively "freezing" the motion of the centrifuge. For example, for a centrifuge arm of about 15 cm at a rotational speed of about 20,000 rpm, the sample movement is about 10 microns during a 30 nano-second burst of radiation. For rotational speeds greater than this, alternate embodiments of the present invention, as described later herein (see FIG. 11), may be employed; these alternate embodiments may also be employed for slower rotational speeds.

A detector means 26, which may be for example, but not limited to a fluorescent screen, may be positioned on the opposite side of the sample holder 18 from X-ray tube 24 so that at least a portion of the X-rays from the X-ray tube 24 that pass through the sample holder 18 and any sample will impinge upon the detector means 26. The detector means 26 may be situated as close to sample holder 18 as possible, to obtain the sharpest image. A fluorescent screen may be, for example, $Gd_2O_2$ S:Pr, made by Eastman Kodak of Rochester, New York, or detector means 26 may be a scintillation crystal such as, for example, but not limited to, NaF.

Alternatively, the detector means 26 may be located to the side of sample holder 18 and moved to its detecting position only after the centrifuge has begun rotation and the holder 18 is in its "rotating" horizontal position, as depicted in FIG. 1. This allows the detector 26 to be much closer to the sample and to minimize any radiation beam dispersion. In a similar manner and for an alternate embodiment of the present invention, the radiation source may be similarly mounted in such a movable fashion and the detector 26 may be fixed above and immediately adjacent the holder 18 in its horizontal position. Alternatively, the radiation source 24 may be permanently mounted below the sample holders 18, and the detector 26 mounted above the rotating position of holders 18, as described later herein (see FIG. 12).

The fluorescent screen material is chosen to have high quantum efficiency for the energy of the incident radiation or X-ray spectrum. In addition, the fluorescent screen must be sufficiently thick to ensure that a substantial portion of the available radiation or X-ray energy is converted to optical energy. In addition, the phosphor is chosen so that the fluorescence from the screen has decayed before the next radiation or X-ray burst is initiated which can be, for example, but not limited to, 1 second later than the preceding burst.

Referring now to FIG. 1A, the presently preferred detector means 26 is depicted. For this detector means 26, a fluorescent screen 27 may be employed to detect radiation and emit light as a result of this detection. The light output from fluorescent screen 27 may be focused by lens 28 or fiber optic cables (not shown) onto an image intensifier 29, such as Model 3603, 25 mm MCP manufactured by Varo, Inc., Electron Devices Division, of Garland, Tex. The region from lens to image intensifier is shrouded by light cover 30 to prevent stray light from entering the assembly. The function of the image intensifier tube is to provide suitable amplification (of up to 100,000 times) so that only a single radiation or X-ray pulse or burst is necessary to obtain a high quality image. The amplified output from the image intensifier tube may be detected by film, a television camera, or a solid state array camera 31, such as the MC 9256-1 model available from EG&G Reticon of Sunnyvale, Calif. The solid state array camera may contain, for example, a 256 by 256 square array of light sensitive photodiodes, or some other type of solid state array, each of which is 25 micrometers square and which are spaced 25 micrometers apart, mounted inside a camera such as the camera discussed hereinabove. The solid state array camera 31 can, in general, have an M by N array of photodiodes. Alternatively, a direct detector of radiation or X-rays in an array arrangement may be employed as detector means 26 to directly detect X-rays, or other types of electromagnetic radiation, without the use of a screen or image intensifier.

In this manner the position of fluids within the sample may be determined at a plurality of points (projections into a two-dimensional detector array). This plurality of points allows for very precise location of fluids and their saturations within the sample, as well as precise detection of movement of these saturations in the sample. The output of the detector may be directed to various storage or recording devices.

Alternatively, another source of pulsed X-rays, such as, for example, but not limited to synchrotron radiation from a cyclotron (not shown), may be employed to irradiate the sample and sample holder. Another alternative embodiment may employ a constant radiation source, (such as, or example, but not limited to a rotating anode X-ray tube) and employ a pulsed or strobed detector to only look at the detector output when the holder and sample is between the radiation source and detector.

Referring now to FIG. 2, there may be seen a schematic block diagram of one embodiment of the apparatus of the present invention. More particularly, computer/controller 52 is depicted interconnected with speed controller 54, strobe controller 56, and analog-to-digital converter 58. The strobe controller 56 provides the strobe pulse to the X-ray tube power supply 60 which energizes or "fires" the X-ray tube 24, which is preferably a flash X-ray tube. The X-rays are depicted as arrows emanating from collimator 25 and passing through sample holder 18 (containing a sample) before being detected by detector 26. The output of detector 26 is supplied to analog-to-digital converter 58, which digitizes the detector's output and then supplies the digitized output to computer/controller 52. There is also an interconnection between the speed controller 54 and the strobe controller 56, which provides for synchronization between these two controllers such that the X-ray tube is "fired" when the appropriate holder 18 and sample is located beneath the X-ray tube. This is accomplished by signals from synchronizing means 22.

The synchronizing means 22 needs to be capable of imaging the sample at the same position independent of the speed of operation of the centrifuge. However, at the highest operating speeds (approximately 20,000 rpm) of the Beckman L8-55M/P, the fixed time delays in the strobe controller and X-ray power supply may cause the X-ray tube to fire too late, resulting in an image of the sample shifted relative to the imaging array. The synchronizing means may be calibrated at each speed to cause the strobe controller to fire earlier as the centrifuge speed is increased, to avoid this shifting of the sample relative to the array.

Computer/controller 52 may be a microcomputer which performs the control functions described hereinbelow as well as providing data storage and real time processing of the output data provided by detector 26. Alternatively, the various control functions may be performed by a separate controller circuit which directs the output from detector 26 to a microcomputer which can then perform the data storage and initial processing.

Speed controller 54 controls the speed at which the rotor 16 of centrifuge 10 of FIG. 1 is rotated by controlling the speed of motor 12. Computer/controller 52 provides a signal to speed controller 54 which indicates the desired rotor speed. Although the rotor may be run at one speed for some preselected period of time and then the speed of the rotor increased in predetermined steps with a fixed period of time allocated at each step, the computer/controller 52 may control speed in any manner desired. Strobe controller 56 provides a predetermined number of strobe pulses to the X-ray tube power supply 60 in response to a control signal from the computer/controller 52.

Solid state camera 31 (see FIG. 1A) may consist of any suitable solid state array, such as for example, but not limited to a photodiode array and associated circuitry mounted in a suitable camera, as is presently preferred. Each of the photodiodes in the two-dimensional array may be connected in parallel with a capacitor which is charged to a predetermined saturation charge. This charge is leaked off by current generated when light impinges on the photodiode. The remaining charge and the voltage across the capacitor is proportional to the amount of light striking the respective photodiode during a fixed exposure time.

The photodiode array is scanned by a digital shift register which sequentially causes the voltage across the respective capacitors in each row, one row at a time, to be sent to a common output line. The capacitor is then refreshed to its original saturation charge and the shift register moves on to the next photodiode in the array. The photodiodes are constantly being scanned and refreshed at a frequency determined by computer/controller 52. When computer/controller 52 determines that it is time to collect a data sample, it waits until the last photodiode in the array has been scanned and refreshed. It then stops the scanning process and signals strobe controller 56 to pulse the X-ray power supply.

Computer/controller 52 then waits a predetermined period of time after the X-ray pulse to ensure collection of sufficient light output from the phosphor screen 27 and it then signals solid state camera 31 to restart the scanning process. It should be noted that the only light that is seen by the photodiode array is the light provided by the fluorescence of the phosphor screen 27, as intensified by image intensifier 29.

The output signal provided by each photodiode and capacitor combination is provided to the common output line by the shift register. The common output line is connected to an analog-to-digital converter 58, which is preferably a part of computer/controller 52, although it may be separate from computer/controller 52. Analog voltages are converted to equivalent digital signals by the analog-to-digital converter 58, which may then be stored and/or processed by computer/controller 52. This digitized output may be directed to a CRT monitor or other visual output devices, such as pen recorders for each row of the array, immediately after the photodiode array has been scanned to provide a visual display of the data.

For a constant radiation source, or constant X-ray source, the outputs of the detector may be ignored until the preselected holder is positioned between the source and detector, as noted by an appropriate signal from computer/controller 52. Then, the detector signal is treated as noted hereinbefore.

Referring now to FIG. 3, there may be seen a simplified block diagram of an alternate embodiment of the apparatus of the present invention. A CRT monitor 74 is shown appropriately connected to computer/controller 52 as described hereinbefore, which may be for example, but not limited to, an IBM PC computer. The CRT monitor is the monitor on which the digitized output may be displayed. Further, the digitized image data may be stored on appropriate storage media 72, which may be for example, but not limited to, a CIPHER tape deck. The computer/controller 52 may also be connected by a high speed serial or parallel port to remote processing computer 70, which may be for example, but not limited to, a VAX 11/785 computer. Computer 70 may then calculate fluid saturations, generate saturation images and may provide animated movies of saturation changes during fluid displacement processes. The calculation of fluid saturations is based upon intensity information obtained as described hereinabove.

Further, computer 70 may be linked to other high-speed computers (not shown), such as for example, but not limited to a CRAY computer. Such a high-speed computer may be employed to calculate numerical simulations of fluid saturations (or other parameters) and their changes for the operating conditions of the centrifuge for various assumed sample characteristics. These assumed sample characteristics may be changed until the numerical simulation gives good agreement to the actual centrifuge data. Then the simulation and centrifuge results may be displayed together, in any suitable format, such as for example, but not limited to, animated movies, video tape, or color CRT displays.

However, to determine fluid saturations, intensity images must be obtained with the core fully saturated with each fluid whose saturation is to be measured. These intensity images (fully saturated core) are used with those from the centrifuging process to compute fluid saturations (based upon Beer's Law, as described later herein) and then to generate saturation images from which animated movies may be made.

It should be noted that the rate at which images can be collected will be determined by the rate at which the analog voltages can be clocked out of the photodiode array and digitized. For an image each second from a 256 by 256 photodiode array with 8 bit resolution, the clocking and digitization rates must exceed $5.25 \times 10^5$/sec (i.e., approximately one-half a megahertz). This can be achieved with standard analog-to-digital electronics as is well known in the art.

Figure 4:
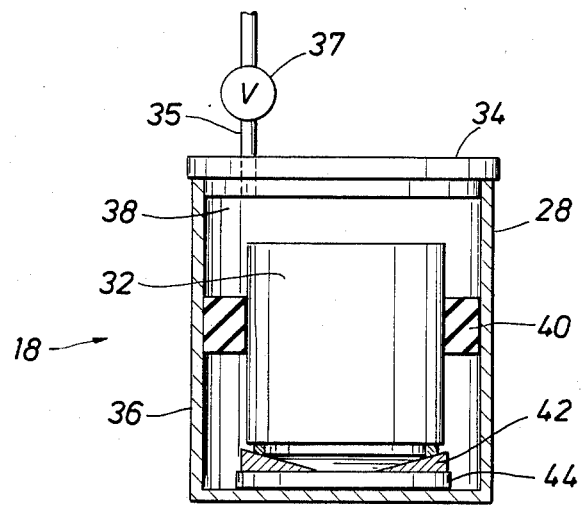
FIG. 4 shows an enlarged cross-section of a portion of the apparatus depicted in FIG. 1.

Referring now to FIG. 4, there may be seen a side view, partially in cross-section, of one embodiment of sample holder 18. This sample holder 18 is adapted for holding a core sample 32 from a downhole core of an oil well. This sample 32 and sample holder 18 is served by way of illustration and not by limitation since the apparatus of the present invention can also be employed to analyze various porous solids, mixtures and fluids, for example, but not limited to soils, concrete or human blood. Sample holder 18 comprises a core housing 36 which has a chamber 38 that is suitably sized to accommodate core sample 32. Core housing 36 is constructed of suitable material to be transparent to the radiation employed, for example, aluminum may be employed for X-ray radiation. Core housing 36 is provided with a lid 34 to facilitate loading and unloading the sample. Lid 34 may have a pressurization port 35 and valve 37 to pressurize the chamber either with an overburden gas or a high pressure displacement gas such as carbon dioxide. A spacer ring 40 is positioned around core sample 32 and a support ring 42 is positioned between the core sample 32 and the bottom of sample holder 18.

Preferably, the sample holder and sample have a precision bore and a square cross section which results in uniform radiation or X-ray path lengths over the entire core sample. Spacer ring 40 can be made of any suitable resilient material which is suitably radiation or X-ray transparent. Support ring 42 has an open volume that allows any ejected fluids to accumulate and be measured after the centrifuging process. A separate collection chamber (not shown) may also be located at the bottom of the sample holder 18, as is known in the art, so that accumulated fluids may also be measured during the centrifuge process.

A reference standard 44 may be included to provide a suitable radiation absorption standard in the image which allows normalization for flux variations. Reference standard 44 may be any suitable material with a known linear attenuation coefficient and good transparency to the radiation employed, such as for example, but not limited to fused quartz for X-ray radiation.

The basic quantity measured by this invention is the linear attenuation coefficient $\mu$. This is defined from Beer's Law, $I/I_o = \exp(-\mu x)$, where $I_o$ is the incident radiation intensity and I is the intensity remaining after passing through a thickness, x, of material having a linear attenuation coefficient, $\mu$. Beer's Law assumes a narrow radiation beam and monochromatic (single energy) radiation. An X-ray tube does not emit monochromatic X-rays, however, but emits X-rays having a spectrum of energies D(E), where D(E) is the relative photon energy between the energies E and E+dE. The mean X-ray energy, $\overline{E}$, of the spectrum D(E) is defined as:

$$\overline{E} = \int_o^{E_{max}} D(E) \, E \, dE / \int_o^{E_{max}} D(E) \, dE$$

where $E_{max}$ is the peak acceleration potential. With no absorbing object (i.e. no sample or holder) between the source and detector, the detector output, $V_o$ is:

$$V_o = K \int_o^{E_{max}} D(E) \, dE$$

where K is the detector proportionality constant. However, after radiation passes through an absorbing object, the detector output V is:

$$V = K \int_o^{E_{max}} D(E) \exp(-\int_1 \mu(r,E) \, dl) \, dE$$

where the inner integral is taken over the path length 1 between source and detector, $\mu(r,E)$ is the spatial and energy dependent linear attenuation coefficient, and K is the detector proportionality constant. Thus, by comparing $V/V_o$, the path integral of $\mu$ may be determined through the material. Since the thickness of the core is known, $\mu$ may be determined for the mean energy of the X-ray beam.

Figure 5:
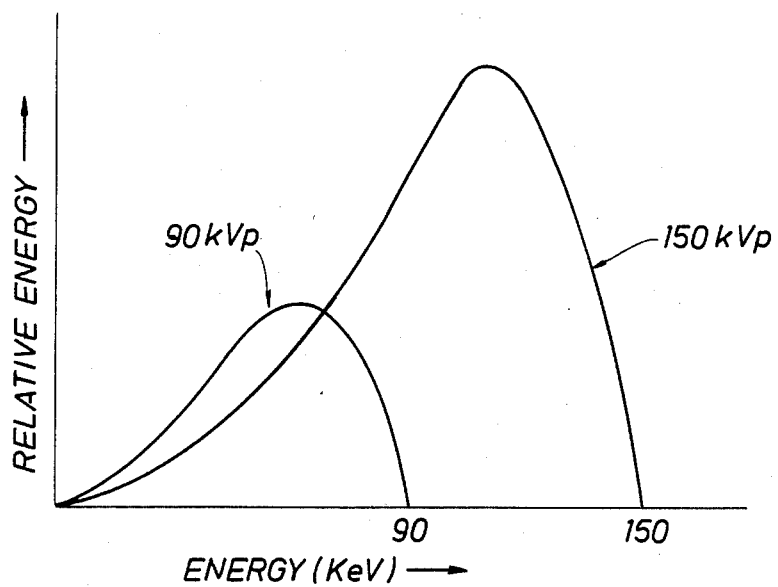
FIG. 5 shows typical X-ray tube spectrum for two different peak acceleration voltages.

Referring now to FIG. 5, there may be seen a depiction of X-ray tube spectra for two different peak acceleration voltages. More particularly, FIG. 5 plots the energy spectrum generated by a typical tungsten target X-ray tube with two different peak acceleration potentials of 90 kilovolts and 150 kilovolts. This Figure demonstrates that the mean energy of an X-ray tube emission spectra may be changed by employing different acceleration potentials, as discussed later herein.

Figure 6:
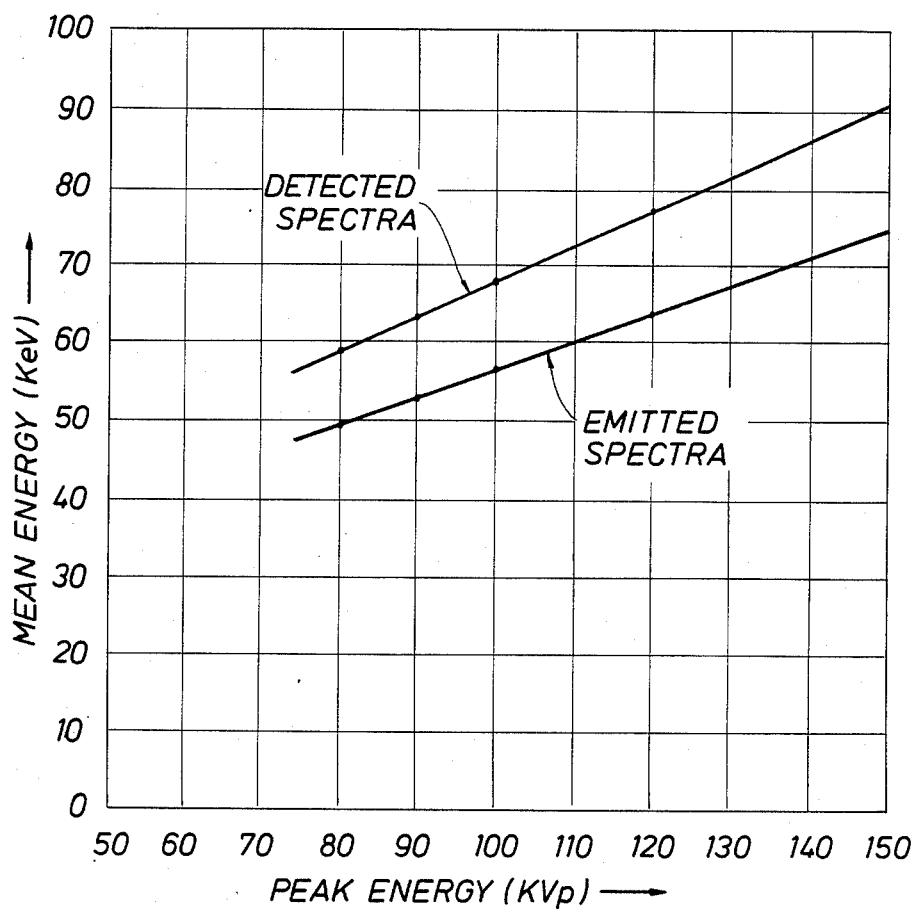
FIG. 6 shows the mean X-ray energy of a typical X-ray tube spectrum as a function of peak acceleration voltage.

Referring now to FIG. 6, there may be seen a depiction of the mean X-ray energy of a typical tungsten target X-ray tube spectrum as a function of peak acceleration voltage. More particularly, FIG. 6 shows the mean beam energies emitted by an X-ray tube as a function of peak accelerating potential with and without the filtration provided by 1.5 inches of aluminum and 2 inches of sandstone with 20 percent porosity. Thus, FIG. 6 illustrates a representative change in the energy spectrum emitted by an X-ray tube caused by passage through a sample and sample holder. Similar curves may be generated for other sources of electromagnetic radiation. For two-phase systems, X-ray absorption measurements need only be made at one X-ray energy to determine linear attenuation coefficients in a plurality of points. These coefficients may then be used to determine fluid saturations at those points. As an example, consider an oil/water mixture at a point, for which two equations may be written:

$$\mu = \mu_w S_w + \mu_o S_o$$

and $$1 = S_w + S_o$$

which may be combined, resulting in one equation:

$$\mu = (\mu_w - \mu_o)S_w + \mu_o, \text{ or } S_w = \frac{\mu - \mu_o}{\mu_w - \mu_o}$$

where $\mu$ is the linear attenuation coefficient actually measured, $\mu_w$ and $\mu_o$ are the attenuation coefficients of water and oil for this sample, respectively (which have already been measured) and $S_w$ and $S_o$ are the calculated saturations of water and oil, respectively. For a two-phase system, one of the phases may be doped with a highly absorbent material to increase the difference between $\mu_w$ and $\mu_o$.

For three-phase systems, at least two independent measurements need to be made to determine the saturations. If two X-ray absorption measurements are made at X-ray energies $E_1$ and $E_2$, two equations result:

$$\mu_1 = \mu_{w1} S_w + \mu_{o1} S_o + \mu_{g1} S_g$$

$$\mu_2 = \mu_{w2} S_w + \mu_{o2} S_o + \mu_{g2} S_g$$

A third equation is also available:

$$1 = S_w + S_o + S_g$$

Here, $\mu_1$ and $\mu_2$ are the linear attenuation coefficients of the sample with multiple phases present at $E_1$ and $E_2$, respectively. The terms $\mu_w$ and $\mu_o$ and $\mu_g$ are the attenuation coefficients of the sample fully saturated, respectively, with each one of the three phases, which have been taken for this example to be water, oil and gas. $S_w$, $S_o$, $S_g$ are the respective saturations of these three phases. The third equation states that the pore volume of the sample is completely filled by some combination of these three phases.

These three equations must be linearly independent in order for there to be a unique solution for the three saturations. The ability to obtain two independent measurements by using two different X-ray energies is based on the fact that X-ray attenuation may depend on density as well as on chemical composition. For energies above about 100 Kev X-rays interact with matter predominantly by Compton scattering, which is dependent upon electron density. For X-ray energies well below 100 Kev, photoelectric absorption becomes dominant. Photoelectric absorption is strongly dependent upon atomic number. The heavier elements have greater photoelectric contribution which increases rapidly as the X-ray energy is lowered. In addition, many of the heavier elements have K-absorption edges near the energy range of about 60 to about 90 Kev.

Figure 7:
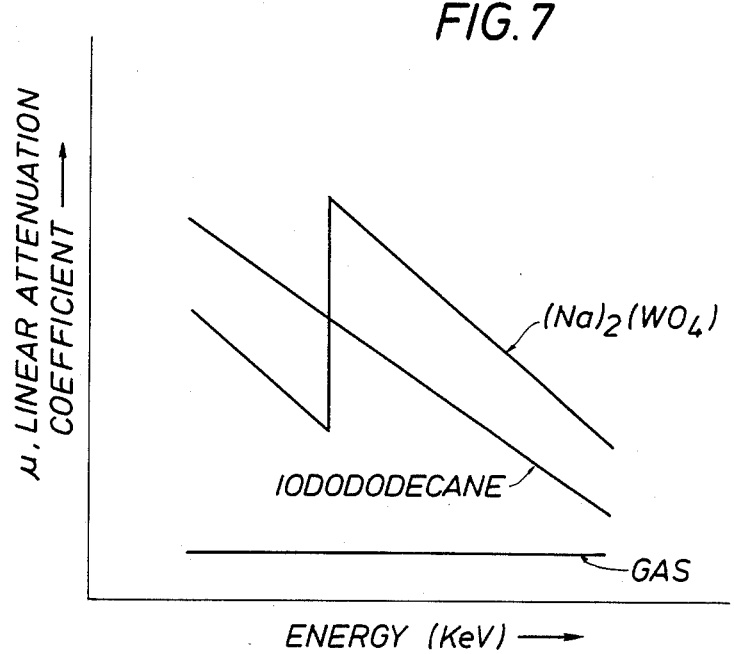
FIG. 7 shows linear attenuation coefficient versus energy for selected dopants.

Referring now to FIG. 7, there may be seen a depiction of the linear attenuation coefficient versus energy for two selected dopants. These two dopants may be placed into the various phases which are in a core sample and used to uniquely identify which phase is absorbing which X-ray energy. The best-conditioned solution (i.e., least sensitive to measurement error) to the foregoing three equations is obtained if two dopants are used, one with a K-absorption edge above the energy $E_2$ and another whose absorption is continuous in this energy range. One dopant is preferably used in each phase and the concentrations are adjusted for maximum sensitivity. An example of dopant and X-ray energy combination that gives good results are $E_1=150$ KVp (92 KeV mean), $E_2=90$ KVp (64 KeV mean), where a water phase is doped with one molar $Na_2WO_4$ and an oil phase is doped with 20 wt% iodododecane. The K-absorption edge for tungsten is about 69.5 KeV; the two energies, $E_1$ and $E_2$ noted hereinbefore, have been selected with one energy just below this K-absorption edge. The 69.5 KeV K-absorption edge is located at approximately the position of the first "o" in "Iodododecane" of FIG. 7. Alternatively, only one phase may need to be doped. For example, if only the oil phase is doped with 20 wt% iodododecane and the same X-ray energies are utilized, good results may still be obtained.

The simultaneous, unique solution to the foregoing three equations is best-conditioned when the radiation at one energy is absorbed primarily by the water phase and the radiation at the other energy is absorbed primarily by the oil phase. In addition, the average absorption levels should be approximately the same at both of these energies. The sensitivity improves with increasing energy spread between the two X-ray energies. However, the low energy scan must still have a high enough X-ray energy to ensure the beam penetrates the sample holder and core without drastic attenuation.

The dual energies needed for three-phase imaging may be achieved by: (1) changing the peak acceleration voltage applied to one X-ray tube, or (2) employing appropriate filters placed in the beam, or (3) employing two X-ray tubes at different voltages, or (4) employing a dual energy detector, or (5) by a combination of any of these methods.

Figure 8:
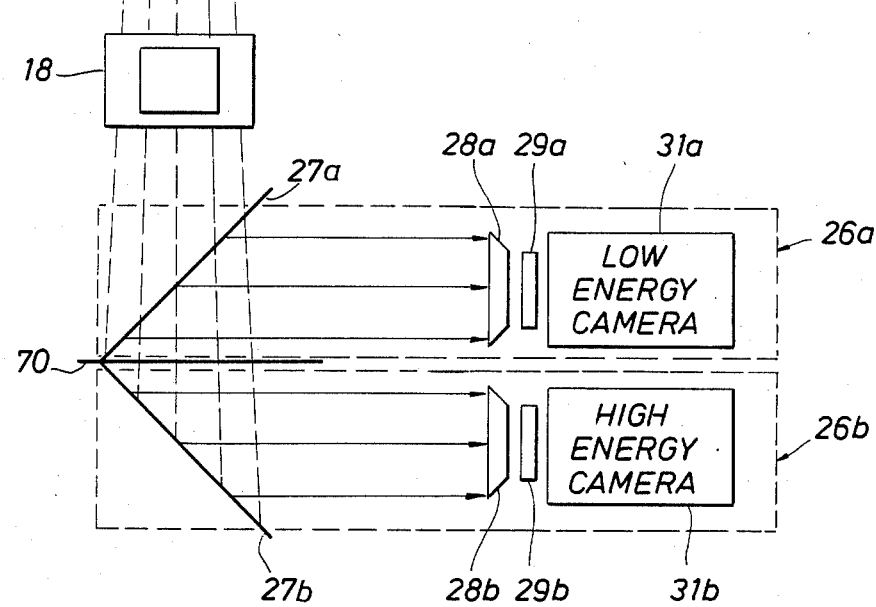
FIG. 8 shows an alternate embodiment of the apparatus of the present invention.

Referring now to FIG. 8, there may be seen a dual energy detection system. FIG. 8 depicts an embodiment of the present invention that uses a single X-ray tube 24 with a single peak acceleration voltage but having dual energy detectors 26a and 26b. FIG. 8 shows a preferred arrangement of dual energy detectors which utilize a low energy phosphor screen 27a such as calcium difluoride and a high energy screen 27b such as sodium iodide, separated by an X-ray filter 70 which passes only high energy X-rays. Photons emitted by the two screens are detected by two separate cameras labeled as the "low energy camera", 31a and the "high energy camera", 31b.

Alternatively, more dopants may be employed if more than three fluids are present. If more dopants are employed more X-ray energies are also required to provide unique well-conditioned solutions to the equations resulting from multiple fluids, as noted hereinbefore.

From the saturation images obtained during the centrifuging process, capillary pressure or relative permeability curves may be rapidly calculated. As a simple example, a sample saturated with water with a density of $\rho_w$ is placed in the centrifuge which is filled with oil with a density $\rho_o$. The sample is spun at an angular velocity $\Omega$ until equilibrium is reached, i.e. no more fluid is produced from the sample. Taking the axis of the centrifuge as the origin, and the axis perpendicular to the axis of the centrifuge as the r axis (directed toward the axis of the centrifuge), the capillary pressure $p_c$ at any location r, spaced from the origin, is $p_c=(\rho_w-\rho_o)\Omega^2(R^2-R^2)$, where R is the distance from the centrifuge axis to the end of the sample most distant from the axis; this equation is similar to one derived by Hassler and Bruner for their centrifuge method. The oil and water saturations at that capillary pressure are obtained from the saturation image at the same location. The centrifuging is repeated at different rotational speeds and the capillary pressure curve for each region of the sample is thus determined.

Similarly, the relative permeability is obtained from two sequential images at the same location separated by a time t. If the core is spun at high angular velocity for early times, then capillary pressure effects are small, compared to the relative permeability. Thus, capillary pressure may be neglected. If the invading phase is assumed to have infinite mobility, the water relative permeability $K_w$ at a location r is:

$$K_w = \frac{\mu_w}{K\Omega^2(\rho_w-\rho_o)r} \int_{r_{in}}^{r} \phi \frac{\partial S_w}{\partial t} dr$$

where the water saturation is $S_w$, $\phi$ is the porosity, K is the permeability, $\mu_w$ is the water viscosity, and $r_{in}$ is the radial distance to the inlet face. This equation is similar to one derived by Hagoort for his centrifuge method. As $S_w$ changes during the centrifuging the relative permeability curve for water can be determined at each location of the sample.

These simple examples are intended to demonstrate that either capillary pressure or relative permeability can be determined at every location throughout the sample using the information available from this invention.

Figure 9:
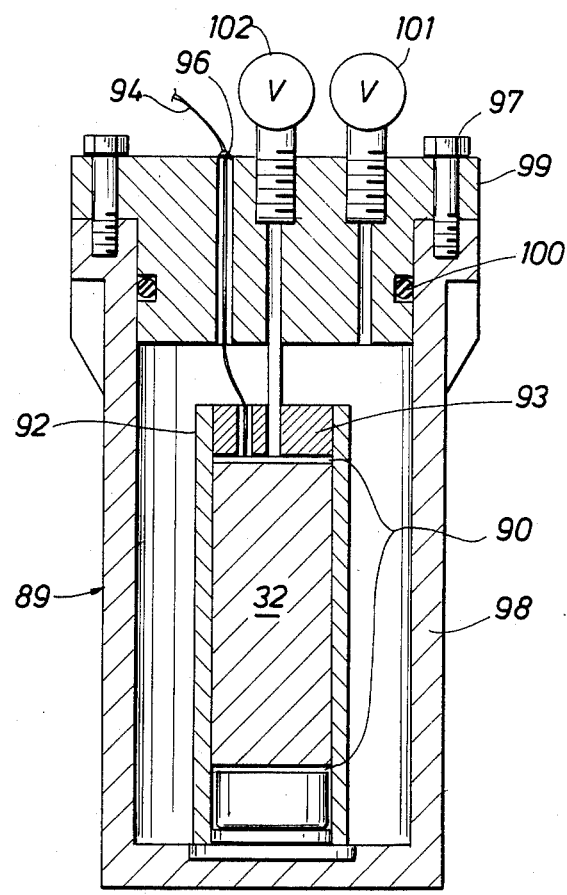
FIG. 9 shows an alternate embodiment of the portion of the apparatus of the present invention depicted in FIG. 4.

Referring now to FIG. 9, there may be seen another sample holder 89 for the X-ray centrifuge of the present invention. This sample holder 89 is adapted for use in this invention to also allow for resistivity measurements with or without overburden pressure during the centrifuging process. This sample holder contains a plurality of electrodes 90 between which the resistivity is measured, mounted on both ends of sample 32. The electrodes 90 may consist of platinized platinum screen to minimize electrode polarization as is well known in the art An overburden sleeve 92 separates the sample 32 from the overburden fluid and also forces electric current to flow only through the sample. The overburden sleeve can be any non-conducting flexible material such as shrink-fit Teflon, rubber, etc. which makes good contact with the sample so that current cannot flow around the exterior surface of the sample. The sample is fitted with an endpiece 93 through which the resistivity lead 94 passes. The sample holder container 98 is fitted with a cap 99 secured by cap bolts 97. An O-ring 100 establishes the high pressure seal between the cap 99 and container 98. A pressure-tight seal 96 is provided in cap 99 for the resistivity lead 94. Container 98 is constructed of appropriate material so as to be effectively transparent to the selected radiation wavelength used to image the sample, such as aluminum for X-ray wavelengths. An overburden valve 101 is used for applying preselected pressure to the overburden fluid before centrifuging. Sample pressure valve 102 is used for applying a preselected pore pressure to the sample before centrifuging. The holder may also have suitable temperature and/or pressure measuring means thereon or therein to allow for measuring the temperature and/or pressure of the sample.

Figure 10A:
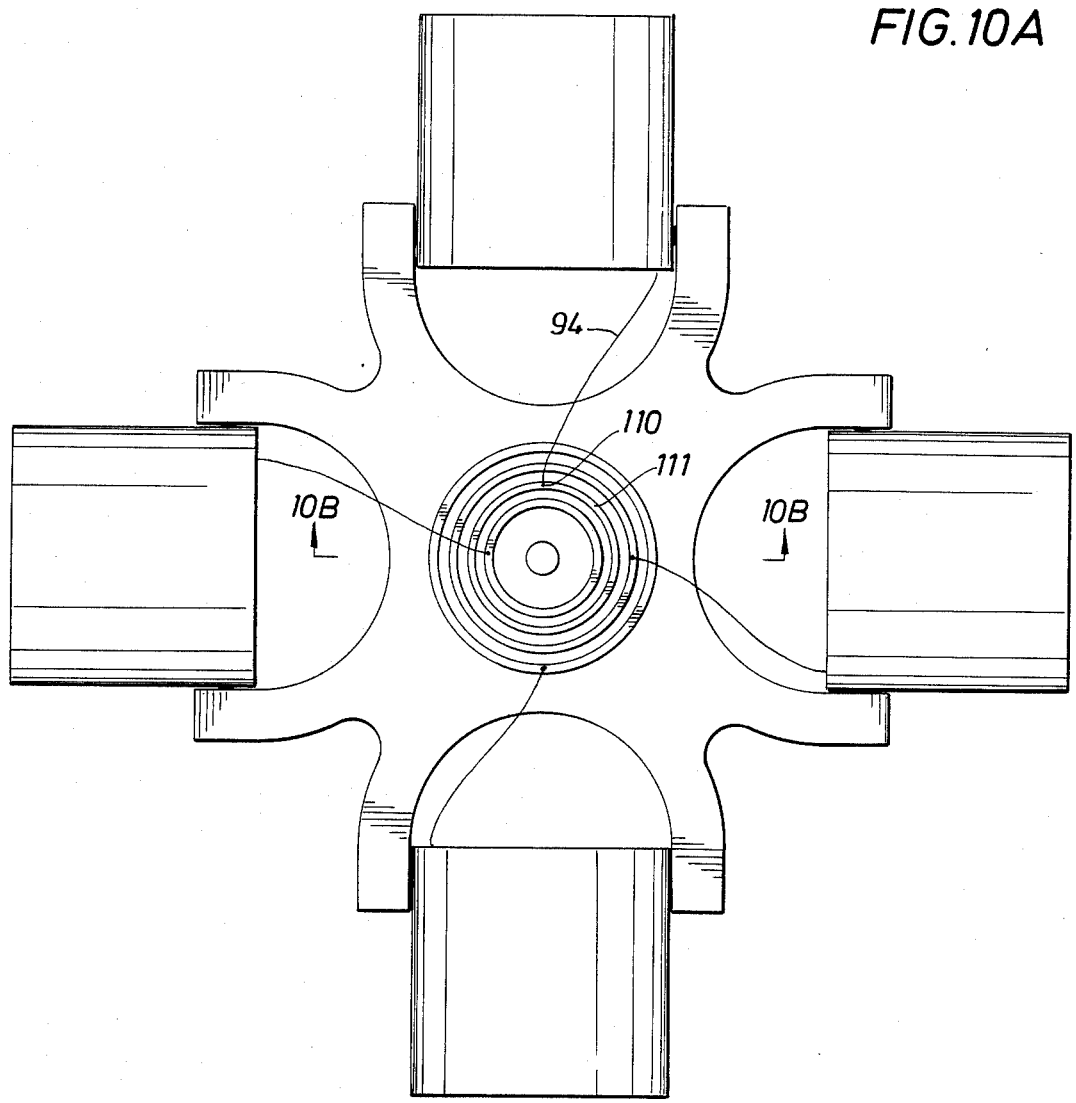
FIGS. 10A and 10B show the apparatus of the present invention employing the embodiment depicted in FIG. 9.
Figure 10B:
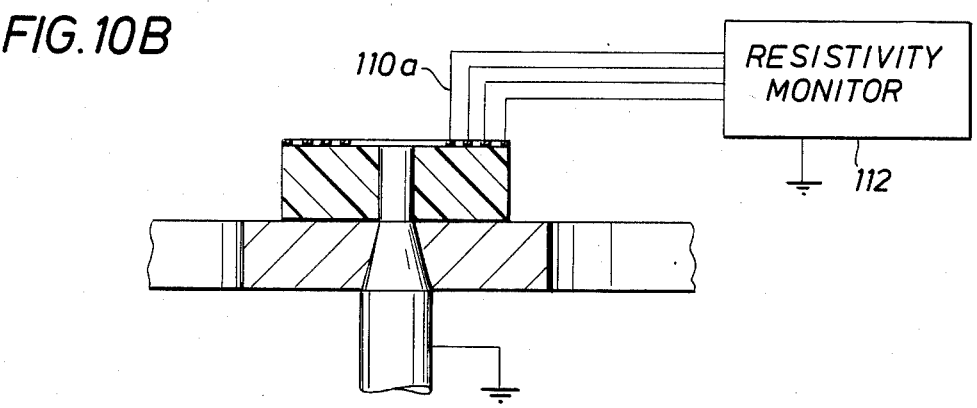

Referring now to FIGS. 10A and 10B, there may be seen a simplified representation of the centrifuge employing the resistivity holder of FIG. 9. More particularly, FIG. 10A shows the electrical connection between the sample holder of FIG. 9 and the resistivity monitoring apparatus. Resistivity lead 94 of FIG. 9 may connect to sliding brush 110 on one of the rotary slip-rings 111; alternatively, lead 94 may be connected electrically to the bottom of one of the slip-rings 111. Electrical ground may be established through one electrode and aluminum fluid collection container 98 to the metal rotor and shaft. Resistivity lead 94 and ground lead connect to resistivity monitor 112, as shown in FIG. 10B, which measures the resistivity across the sample, through a sliding brush 110a and ground wire. The resistivity readings from monitor 112 are stored in computer/controller 52 along with the saturation images.

The sample may be initially saturated with electrically conductive brine of known resistivity. During centrifuging the brine is displaced with nonconductive gas or oil and the sample resistivity increases. Alternatively, the centrifuging can be done in the imbibition mode with brine displacing nonconductive fluid. By combining the resistivity measurements with the saturation images in computer/controller 52 the resistivity versus saturation curve is obtained for either drainage or imbibition cycles. An important advantage of this invention is that the saturation distribution down the core sample is known from the saturation images so that the resistivity curve may be corrected for the effects of non-uniform saturation caused by capillary end effects, as is known in the art.

Figure 11:
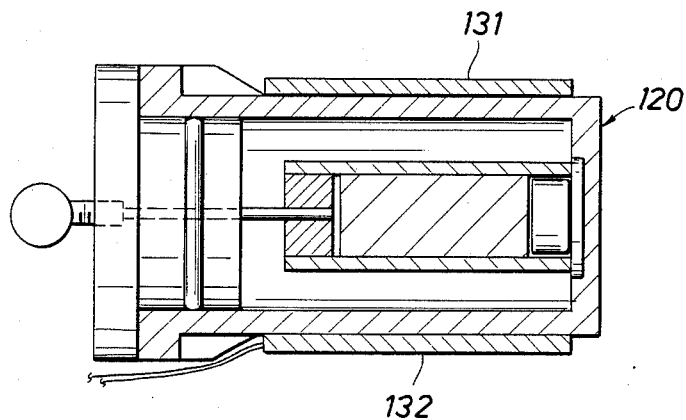
FIG. 11 shows another alternate embodiment of the apparatus of the present invention.

Referring now to FIG. 11, there may be seen an alternative embodiment of the present invention. For this embodiment the sample holder 120 is modified to contain thereon both the electromagnetic radiation source 131 and detector 132. This embodiment is not limited to a particular rotational speed of the centrifuge. More particularly, holder 120 has a radioactive source 131 and solid state array detector 132 mounted on opposite sides of a preferably square holder 120. Source 131 may be for example, but not limited to, an Americium 241 line source. Alternate gamma-ray sources may also be employed in other embodiments of the present invention. Other embodiments may employ a radioactive sample as the source of electromagnetic radiation, or a radioactive source may be included in the fluids used in the sample. Electrical slip rings may be employed to carry the signals from detector 132 to computer/controller 52 for processing, as described hereinbefore. Detector 132 may be a phosphor screen and photodiode array, as noted hereinbefore, or a solid state gamma-ray detector. In this embodiment, the radiation source and detector rotate with the sample to provide continuous data on fluid displacement and a strobed radiation system as described hereinbefore may not be needed, although it may also be used. By combining the continuous (mounted horizontally) and strobed (mounted vertically) features of the present invention, it is possible to construct images of the sample in three dimensions.

Figure 12:
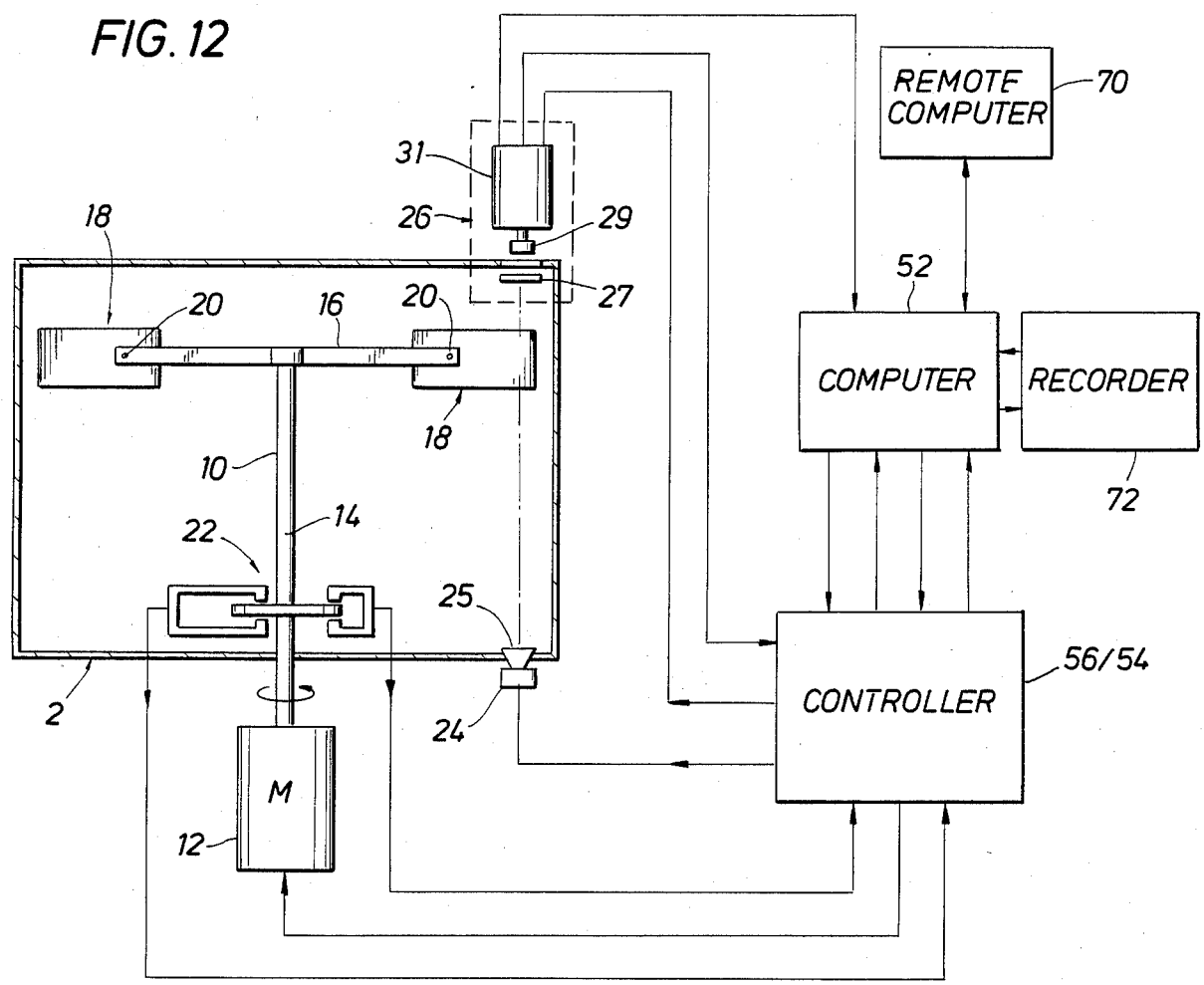
FIG. 12 shows yet another alternate embodiment of the apparatus of the present invention.

Referring now to FIG. 12, there may be seen an alternative embodiment of the present invention. This embodiment is in essence the embodiment depicted in FIG. 1, but with the radiation source 24 now located below the sample holder 18 and the detector means 26 (screen 27, image intensifier 29, and camera 31) located immediately above sample holder 18, when sample holder 18 is in its "rotating" horizontal position. This embodiment also illustrates that the speed 54 and strobe 56 controller may be combined into one controller 56/54.

The apparatus of the present invention may be suitably employed to image a core sample from an earth formation undergoing various enhanced oil recovery techniques, such as, for example, but not limited to $CO_2$, steam and caustic recovery techniques. These samples can be exposed to high pressure and temperature representative of the reservoir conditions during such imaging, as noted hereinbefore. Such imaging provides valuable information on the actual fluid displacement processes occurring in the sample. Further, such images may be compared to images created by numerical simulations run in a high-speed computer, as described hereinbefore. This comparison may be through animated movies, video tape, or color CRT displays. Further, the apparatus may be employed to determine variations in fluid flow properties throughout inhomogeneous samples. This eliminates any assumption of homogeneous fluid flow through a sample, and allows for the observation of any preferential channels or fractures in the sample.

Many other variations and modifications may be made in the apparatus and techniques hereinbefore described by those having experience in this technology without departing from the concept of the present invention. Accordingly, it should be clearly understood that the apparatus and method depicted in the accompanying drawings and referred to in the foregoing description are illustrative only and are not intended as limitations on the scope of the invention.

What is claimed is:

1. A method, comprising:

centrifuging a porous sample containing at least one fluid therein;

periodically imaging at least the entirety of said sample in a plurality of points during centrifuging; and determining the distribution of said at least one fluid for said plurality of points in said sample from said step of periodically imaging.

2. A method as described in claim 1, wherein said imaging comprises illuminating said sample with at least one preselected electromagnetic energy.

3. A method for measuring the distribution of fluids in a porous sample, comprising:

centrifuging said sample, and periodically illuminating said sample with at least two preselected electromagnetic energies and measuring fluid distributions in a plurality of points of said sample during centrifuging.

4. A method for measuring the the distribution of fluids in a porous sample, comprising:

centrifuging said sample, periodically imaging said sample in a plurality of points during centrifuging, and measuring the resistivity of said sample during said centrifuging.

5. A method as described in claim 4, further comprising calculating a resistivity versus saturation curve for said sample based upon said measured fluid distributions.

6. A method as described in claim 5, further comprising correcting said resistivity versus saturation curve for capillary end effects based upon said imaging.

7. A method for measuring the distribution of fluids in a porous sample, comprising:

centrifuging said sample, periodically imaging said sample in a plurality of points during centrifuging, and subjecting said sample to pressure during said centrifuging.

8. A method as described in claim 7, wherein said sample is subjected to overburden pressure.

9. A method as described in claim 7, wherein said sample is subjected to fluid pressure from an injected fluid.

10. A method for measuring the distribution of fluids in a porous sample, comprising:

centrifuging said sample, periodically imaging said sample in a plurality of points during centrifuging, and visually displaying said distribution of fluids in said sample.

11. A method for measuring the distribution of fluids in a porous sample, comprising:

centrifuging said sample, periodically imaging said sample in a plurality of points during centrifuging, and calculating fluid saturations at said plurality of points.

12. A method as described in claim 11, further comprising generating an animated movie of changes in fluid saturations.

13. A method as described in claim 12, further comprising comparing said generated animated movie with a computer-generated numerical simulation animated movie of predicted changes in fluid saturations.

14. Apparatus for measuring the distribution of fluids in a porous sample, comprising:

a centrifuge having a predetermined number of sample holders for containing said sample and capable of operating at a plurality of speeds;

a source of electromagnetic energy positioned to radiate onto at least one preselected holder as it passes adjacent said source;

a detector array positioned to detect electromagnetic energy transmitted through said at least one preselected holder;

synchronizing means for preselecting said at least one preselected holder;

recorder means for recording signals from said detector array; and controller means for controlling said synchronizing means, said recorder means, and the operating speed of said centrifuge.

15. An apparatus as described in claim 14, wherein said source of electromagnetic energy is an X-ray tube.

16. An apparatus as described in claim 15, wherein said X-ray tube is a flash X-ray tube.

17. An apparatus as described in claim 15, wherein said X-ray tube is a constant source X-ray tube.

18. An apparatus as described in claim 17, wherein said constant source X-ray tube is a rotating anode X-ray tube.

19. An apparatus as described in claim 14, wherein said source of electromagnetic energy is synchotron radiation from a cyclotron.

20. Apparatus for measuring the distribution of fluids in a porous sample, comprising:

a centrifuge having a predetermined number of sample holders for containing said sample and capable of operating at a plurality of speeds;

a source of electromagnetic energy positioned adjacent at least one preselected holder to irradiate said preselected holder; and a detector array positioned adjacent said at least one preselected holder and opposite said source to detect electromagnetic energy transmitted through said at least one preselected holder.

21. The apparatus of claim 20, wherein said source of electromagnetic energy is a radioactive nuclide in said fluids.

22. The apparatus of claim 20, wherein said source of electromagnetic energy is a radioactive sample.

23. Apparatus for measuring the distribution of fluids in a porous sample, comprising:

a centrifuge having a predetermined number of sample holders for containing said sample and capable of operating at a plurality of speeds;

a source of electromagnetic energy in at least one of said fluids in said sample located in a preselected sample holder; and a detector array positioned adjacent said preselected sample nolder to detect electromagnetic radiation from said source.

24. A method for measuring the linear attenuation coefficient of a fluid in a porous sample, comprising:

centrifuging said sample;

periodically imaging said sample in a plurality of points during centrifuging; and calculating the linear attenuation coefficient in functional relationship with the thickness of said sample.

25. A method for determining the relative permeability curve of a porous sample, comprising:

centrifuging said sample;

periodically imaging said sample in a plurality of points during said centrifuging;

determining fluid saturations at said plurality of points in functional relationship with time;

determining relative permeability at said plurality of points; and generating a relative permeability curve versus saturation based upon the relative permeability determined at said plurality of points.

26. A method for determining the capillary pressure curve for a porous sample, comprising:

centrifuging said sample at a preselected speed;

periodically imaging said sample in a plurality of points during said centrifuging;

determining fluid saturations at said plurality of points;

determining the capillary pressure curve versus saturation at said plurality of points; and centrifuging said sample at a different preselected speed.

* * * * *